(12) United States Patent
Hallinan et al.

(10) Patent No.: US 9,051,258 B2
(45) Date of Patent: Jun. 9, 2015

(54) PROCESS FOR THE MANUFACTURE OF ACETIC ACID

(71) Applicant: LyondellBasell Acetyls, LLC, Houston, TX (US)

(72) Inventors: Noel C. Hallinan, Loveland, OH (US); John D. Hearn, Beach City, TX (US); Michael E. Fitzpatrick, League City, TX (US); Miraj S. Patel, Sugar Land, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 278 days.

(21) Appl. No.: 13/720,539

(22) Filed: Dec. 19, 2012

(65) Prior Publication Data

US 2013/0190531 A1 Jul. 25, 2013

Related U.S. Application Data

(63) Continuation-in-part of application No. 13/713,930, filed on Dec. 13, 2012.

(60) Provisional application No. 61/578,705, filed on Dec. 21, 2011, provisional application No. 61/578,709, filed on Dec. 21, 2011.

(51) Int. Cl.
    *C07C 51/42* (2006.01)
    *C07C 51/44* (2006.01)
    *C07C 51/12* (2006.01)
    *C07C 51/48* (2006.01)

(52) U.S. Cl.
    CPC .............. *C07C 51/44* (2013.01); *C07C 51/12* (2013.01); *C07C 51/48* (2013.01)

(58) Field of Classification Search
    CPC .......... C07C 51/12; C07C 51/44; C07C 51/48
    See application file for complete search history.

(56) References Cited

U.S. PATENT DOCUMENTS

| | | | |
|---|---|---|---|
| 2,250,976 A * | 7/1941 | Dijck | 208/317 |
| 4,102,922 A | 7/1978 | Price | |
| 4,954,260 A * | 9/1990 | Ludmer et al. | 210/634 |
| 5,001,259 A | 3/1991 | Smith et al. | |
| 5,026,908 A | 6/1991 | Smith et al. | |
| 5,144,068 A | 9/1992 | Smith et al. | |
| 5,371,286 A | 12/1994 | Blay et al. | |
| 5,599,976 A | 2/1997 | Scates et al. | |
| 5,625,095 A | 4/1997 | Miura et al. | |
| 5,723,660 A | 3/1998 | Morimoto et al. | |
| 5,783,731 A | 7/1998 | Fisher et al. | |
| 5,817,869 A | 10/1998 | Hinnenkamp et al. | |
| 5,932,764 A | 8/1999 | Morris et al. | |
| 6,143,930 A | 11/2000 | Singh et al. | |
| 6,339,171 B1 | 1/2002 | Singh et al. | |
| 6,552,221 B1 | 4/2003 | Hallinan et al. | |
| 7,208,624 B2 | 4/2007 | Scates et al. | |
| 7,619,113 B2 | 11/2009 | Powell | |
| 7,790,919 B2 | 9/2010 | Hallinan et al. | |
| 7,790,920 B2 | 9/2010 | Brtko et al. | |
| 7,812,191 B2 | 10/2010 | Hallinan et al. | |
| 7,838,701 B2 | 11/2010 | Trueba et al. | |
| 7,855,306 B2 * | 12/2010 | Zinobile et al. | 562/608 |
| 2010/0228051 A1 | 9/2010 | Key et al. | |

FOREIGN PATENT DOCUMENTS

EP    487284 A2    5/1992
EP    506240 A2    9/1992

OTHER PUBLICATIONS

PCT/US2012/070678 International Search Report and Written Opinion mailed Apr. 19, 2013.

* cited by examiner

*Primary Examiner* — Paul A Zucker

(57) ABSTRACT

The phase separation in the decanter of a process for producing acetic acid by carbonylating methanol in the presence of a catalyst under low water-high acid conditions is facilitated and expedited by forming a liquid mixture (D) which has a water content of at most 10% by weight, based on the weight of the liquid mixture, an acetic acid content of at least 10% by weight, based on the weight of the liquid mixture, and a weight ratio of methyl iodide to methyl acetate of at least 1.5:1, and partitioning the liquid mixture at a temperature of from 0 to 35° C.

17 Claims, 3 Drawing Sheets

PROCESS FOR THE MANUFACTURE OF ACETIC ACID

CROSS REFERENCE TO RELATED APPLICATIONS

This application claims benefit of priority to U.S. Non-Provisional Application Ser. No. 13/713,930 filed on Dec. 13, 2012, U.S. Provisional Application No. 61/578,709 filed on Dec. 21, 2011; and, U.S. Provisional Application No. 61/578,705 filed on Dec. 21, 2011, all of which are incorporated herein by reference in their entirety.

TECHNICAL FIELD

The disclosure relates to an improved process for producing acetic acid by carbonylating methanol in the presence of a catalyst. More particularly, the disclosure relates to a process which improves the phase separation of a condensed light ends overhead stream in cases where the overhead stream comprises high amounts of acetic acid and low amounts of water.

BACKGROUND OF THE DISCLOSURE

The manufacture of acetic acid by carbonylating methanol in the presence of a catalyst is of major industrial importance as acetic acid is employed in a wide variety of applications. While the reaction per se can be represented by

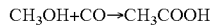
$$CH_3OH + CO \rightarrow CH_3COOH$$

the underlying chemistry is intricate and involves a multiplicity of interrelated reactions, by-products, and equilibria. To be practicable, a manufacturing process, therefore, has to balance those reactions, the associated by-products, and the purification of the product.

Prior to 1970, acetic acid was produced using a cobalt catalyst. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One of the problems associated with the original Monsanto process is that a large amount of water (about 14% by weight of the reaction mixture) is needed to produce hydrogen in the reactor via the water-gas shift reaction

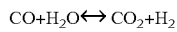
$$CO + H_2O \leftrightarrow CO_2 + H_2$$

Water and hydrogen are necessary to react with precipitated Rh(III) and inactive $[Rh_4(CO)_2]$ to regenerate the active Rh(I) catalyst. However, a large amount of water increases the formation of hydrogen iodide which, in turn, increases the formation of undesired by-products, such as long chain alkyl iodides, which are hard to separate from the acetic acid product. Further, removing a large amount of water from the acetic acid product renders the process more costly.

In the late '70s Celanese modified the carbonylation process by introducing lithium iodide to the reaction mixture. Lithium iodide increases the catalyst stability by minimizing side reactions which produce inactive Rh(III) species. Consequently, the amount of water which is necessary to stabilize the catalyst can be reduced. Additionally, lithium iodide has been found to decrease the vaporization tendency of water, see, e.g., EP 506 240. The process, thus, has advantages with regard to the separation of water and acetic acid.

It has been discovered that catalyst stability and the productivity of the carbonylation reactor can be maintained at surprisingly high levels, even at very low water concentrations, i.e. 4%-wt. or less, in the reaction medium (despite the general industrial practice of maintaining approximately 14 wt. % or 15 wt. % water) by maintaining in the reaction medium, along with a catalytically effective amount of rhodium, at least a finite concentration of water, methyl acetate and methyl iodide, a specified concentration of iodide ions over and above the iodide content that is present as methyl iodide or other organic iodide. By using relatively high concentrations of the methyl acetate and iodide salt, a surprising degree of catalyst stability and reactor productivity has been achieved even when the water content of the liquid reaction medium is as low as about 0.1 wt. %, see, e.g., U.S. Pat. No. 5,001,259, U.S. Pat. No. 5,026,908 and U.S. Pat. No. 5,144,068. However, although the low water carbonylation process for the production of acetic acid reduces such by-products as carbon dioxide, hydrogen, and propionic acid, the amount of other impurities, present generally in trace amounts, is increased, and the quality of acetic acid sometimes suffers when attempts are made to increase the production rate by improving catalysts, or modifying reaction conditions.

Typically, acetic acid is produced in a plant which can be conveniently divided into three functional areas, i.e., the reaction, the light ends recovery, and the purification. In general, the reaction area comprises a reactor or reaction zone and a flash tank or flash zone. The light ends recovery area comprises a light ends distillation column or fractioning zone (also referred to in the art as "splitter" or "splitter column") and a partitioning zone or phase separation vessel, e.g., a decanter. The light ends distillation column may also be part of the purification area, which in turn further comprises a drying column and optionally a heavy ends distillation column, see, e.g., U.S. Pat. No. 6,552,221.

The light ends recovery area inter alia serves to separate undesired by-products such as alkanes, carbonyl impurities, and alkyl iodide impurities. The overhead stream which is recovered from the light ends distillation column is condensed and phase separated in the decanter to obtain a light, aqueous phase comprising primarily acetic acid and water, and a heavy, organic phase comprising primarily methyl iodide, methyl acetate, and alkane impurities. The aqueous phase which is obtained in this manner can be treated to remove acetaldehyde and other carbonyl impurities before being recycled, e.g., to the light ends distillation column, see, e.g., U.S. Pat. No. 5,599,970, U.S. Pat. No. 5,625,095, U.S. Pat. No. 5,732,660, U.S. Pat. No. 5,783,731, U.S. Pat. No. 6,143,930, EP 0 487 284. The organic phase can be further purified to remove, e.g., the alkane impurities, and at least part of the purified methyl iodide is returned to the process, see, e.g., U.S. Pat. No. 4,102,922, U.S. Pat. No. 5,371,286, U.S. Pat. No. 5,723,660, and U.S. Pat. No. 7,812,191.

The proper operation of the decanter is a critical part of the overall performance of the acetic acid process. The partitioning time, i.e., the time which is necessary to achieve separation of the organic and the aqueous phase in the decanter, must be shorter than the residence time of the mixture to be phase separated in the decanter in order to ensure sufficient recycle of the methyl iodide promoter to the reaction zone which, in turn, ensures that the reaction rate in the reaction zone is maintained. If the phase separation in the decanter is incomplete, the methyl iodide phase which is recovered from the decanter is diluted. Recycling of the diluted methyl iodide causes destabilization of the reactor conditions manifested by, e.g., upset of the water balance in the reactor;
increased energy consumption;

decreased reaction rate; and
increased catalyst consumption.

Additionally, dilution of the methyl iodide phase alters its density which interferes with the operation of downstream pumps and other in-line equipment.

However, as the water concentration in the reaction mixture is lowered (also referred to as "low water-high acid" or "low-water" conditions) and the methyl acetate concentration increases, the vapor load of the light ends distillation column increases which, in turn, causes a high carry-over of acetic acid into the decanter. The solubility of acetic acid in both the methyl iodide and the aqueous phase causes the phase separation to deteriorate, eventually resulting in a single liquid phase in the decanter. When this condition occurs, the stream which is returned from the decanter to the light ends column includes a high amount of methyl iodide as well as impurities. The presence of this additional methyl iodide and impurities further interferes with the ability of the light ends column to cleanly separate light ends materials such as methyl acetate and impurities from the acetic acid product. Thus, the failure of the condensed light ends overhead to separate into two phases in the decanter under low water-high acid process conditions interferes with the removal of undesired by-products from the process. Also, when this condition occurs, the amount of methyl iodide promoter which is recycled from the decanter to the reaction zone is reduced due to dilution which, in turn, is detrimental for the reaction rate.

The problem of efficient and thorough phase separation in the decanter under low-water process conditions is known in the art and attempts have been made to ensure proper phase separation of the condensed overhead stream in the decanter. For example, U.S. Pat. No. 5,723,660 proposes to significantly reduce the temperature to which the light ends overhead is cooled before it enters the decanter, to batch-wise feed water into the light ends column, or to conduct multiple distillations to ensure that the methyl acetate concentration remains below 40 weight percent. It is illustrated, however, that cooling of the condensed overhead stream, even to temperatures below 0° C., can be insufficient to achieve phase separation. On the other hand, conducting multiple distillations to reduce the concentration of methyl acetate increases the process steps, thus increasing the expenditure. Also, feeding water into the light ends column is likely to significantly alter the water balance throughout the process each time water is added.

Accordingly, there continues to be a need to further improve the manufacture of acetic acid under low water-high acid conditions. In particular, there continues to be a need to improve and stabilize the phase separation in the decanter to ensure stable reactor conditions as well as continuous and reliable removal of impurities.

SUMMARY OF THE DISCLOSURE

In general, the present disclosure provides a process for producing acetic acid. In one embodiment, the process for producing acetic acid comprises the steps of: (1) reacting the starting materials in a reaction zone to form a reaction mixture comprising acetic acid, methyl acetate, methyl iodide, a catalyst and water; and (2) separating the reaction mixture comprising acetic acid into a vapor stream that comprising acetic acid into a vapor stream that comprises acetic acid and a liquid stream; (3) separating the vapor stream into a product stream comprising an acetic acid and water mixture and an overhead stream; (4) condensing the overhead stream to form a liquid mixture at a temperature between 0 and 35° C.; and, (5) partitioning the liquid mixture into a light, aqueous phase and heavy organic phase.

In a first aspect, the present disclosure relates to a process for producing acetic acid which comprises:
(a) carbonylating methanol in the presence of a catalyst in a reaction zone to obtain a reaction mixture (A) comprising acetic acid, methyl acetate, methyl iodide, the catalyst, and water;
(b) separating at least a part of the reaction mixture (A) in a flash zone to obtain a liquid stream ($B_L$) comprising the catalyst, and a vapor stream ($B_V$) comprising acetic acid, methyl acetate, methyl iodide, and water, and withdrawing the vapor stream ($B_V$) from the flash zone;
(c) separating the vapor stream ($B_V$) in a fractioning zone to obtain a product stream ($C_P$) comprising acetic acid and a minor amount of water, and an overhead stream ($C_O$) comprising acetic acid, methyl acetate, methyl iodide, and water,
(d) condensing the overhead stream ($C_O$) and forming a liquid mixture (D) which has a water content of at most 10% by weight, an acetic acid content of at least 10% by weight, and which comprises methyl iodide and methyl acetate in a weight ratio of methyl iodide to methyl acetate of at least 1.5:1,
(e) partitioning the liquid mixture (D) in a partitioning zone to obtain a light, aqueous phase ($D_A$) comprising acetic acid, and water, and a heavy, organic phase ($D_O$) comprising methyl iodide, and methyl acetate; wherein the liquid mixture (D) is partitioned at a temperature of from 0 to 35° C.

In a second aspect, the present disclosure provides for a process in accordance with the foregoing aspect, wherein the temperature of the liquid mixture (D) is from 5 to 30° C.

In a third aspect, the present disclosure provides for a process in accordance with either one of the foregoing aspects, wherein the temperature of the liquid mixture (D) is at most 27° C.

In a fourth aspect, the present disclosure provides for a process in accordance with either one of the foregoing aspects, wherein the water present is the liquid mixture is innate water.

In a fifth aspect, the present disclosure provides for a process in accordance with either one of the foregoing aspects, wherein the liquid mixture (D) comprises from 0.1 to 8.5% by weight of water.

In a sixth aspect, the present disclosure provides for a process in accordance with either one of the foregoing aspects, wherein the liquid mixture (D) comprises at most 7.5% by weight of water.

In a seventh aspect, the present disclosure provides for a process in accordance with either one of the foregoing aspects, wherein the liquid mixture (D) comprises at least 15% by weight of acetic acid.

In an eighth aspect, the present disclosure provides for a process in accordance with either one of the foregoing aspects, wherein the weight ratio of methyl iodide to methyl acetate in the liquid mixture (D) is at least 2:1.

In a ninth aspect, the present disclosure provides for a process in accordance with either one of the foregoing aspects, wherein the liquid mixture (D) comprises at most 35% by weight of methyl acetate.

In a tenth aspect, the present disclosure provides for a process in accordance with either one of the foregoing aspects, wherein the liquid mixture (D) comprises at least 30% by weight of methyl iodide.

In an eleventh aspect, the present disclosure provides for a process in accordance with either one of the foregoing aspects, wherein the liquid mixture (D) comprises
(i) from 30 to 84.9% by weight of methyl iodide,
(ii) from 10 to 25% by weight of acetic acid,
(iii) from 5 to 35% by weight of methyl acetate, and
(iv) from 0.1 to 10% by weight of water,
the weight percentages in each case being based on the total weight of the components (i) to (iv).

In a twelfth aspect, the present disclosure provides for a process in accordance with either one of the foregoing aspects, wherein the weight ratio of methyl iodide to methyl acetate of the liquid mixture (D) is provided by adding to $C_O$ extraneous or innate methyl iodide.

In a thirteenth aspect, the present disclosure provides for a process in accordance with either one of the foregoing aspects, further comprising separating the partitioned phases $D_A$ and $D_O$ to obtain an aqueous stream ($E_A$) and an organic stream ($E_O$), and providing the weight ratio of methyl iodide to methyl acetate of D by directly or indirectly recycling at least a part of the organic stream ($E_O$) to step (d).

In a fourteenth aspect, the present disclosure provides for a process in accordance with either one of the foregoing aspects, which comprises separating at least a part of the organic stream ($E_O$) to obtain an overhead product ($F_O$) comprising methyl iodide, and a bottom product ($F_B$) comprising acetic acid, methyl acetate, and water, and recycling at least a part of the overhead product ($F_O$) to step (d).

In a fifteenth aspect, the present disclosure provides for a process in accordance with either one of the foregoing aspects, wherein the partitioning zone is equipped with external or internal cooling means.

In a sixteenth aspect, the present disclosure provides for a method of expediting the phase separation of a liquid mixture comprising at least 10% by weight of acetic acid, at least 5% by weight of methyl acetate, at least 20% by weight of methyl iodide and at most 10% by weight of water, which comprises
(a) reducing the temperature of the liquid mixture, and/or
(b) adjusting the weight ratio of methyl iodide and methyl acetate in the liquid mixture to a weight ratio of methyl iodide to methyl acetate of at least 1.5:1.

In a seventeenth aspect, the present disclosure provides for a process in accordance with the foregoing sixteenth aspect, wherein the temperature of the liquid mixture is reduced to be of from 0 to 35° C.

In an eighteenth aspect, the present disclosure provides for a process in accordance with either one of the foregoing aspects fifteen and sixteen, wherein the weight ratio of methyl iodide and methyl acetate is adjusted by adding appropriate amounts of methyl iodide to the liquid mixture.

In a nineteenth aspect, the present disclosure provides for a process in accordance with either one of the foregoing aspects sixteen to eighteen, wherein the liquid mixture comprises at most 8.5% by weight of water.

BRIEF DESCRIPTION OF THE DRAWINGS

For a more complete understanding of the present invention, reference is now made to the following descriptions taken in conjunction with the accompanying drawings.

DETAILED DESCRIPTION OF THE DISCLOSURE

Figure 1:
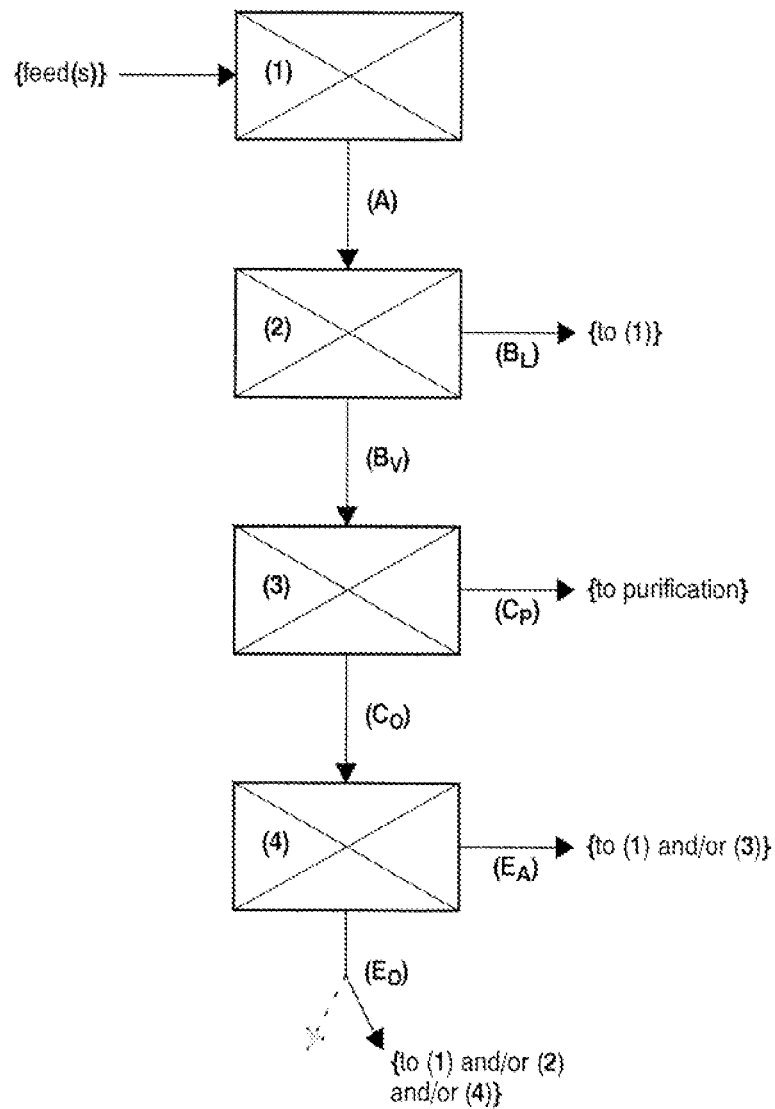
FIG. 1 shows a flow-chart schematically illustrating the flow of the stream(s) involved in the process according to the present disclosure.

A detailed description of embodiments of the present process is disclosed herein. However, it is to be understood that the disclosed embodiments are merely exemplary of the process and that the process may be embodied in various and alternative forms of the disclosed embodiments. Therefore, specific procedural, structural and functional details which are addressed in the embodiments disclosed herein are not to be interpreted as limiting, but merely as a basis for the claims and as a representative basis for teaching one skilled in the art to variously employ the present process.

Unless specifically stated otherwise, all technical terms used herein have the meaning as commonly understood by those skilled in the art.

The designation of groups of the Periodic Table of the Elements as used herein is in accordance with the current IUPAC convention.

Moreover, unless specifically stated otherwise, the following expressions as used herein are understood to have the following meanings The expression "liquid stream" as used herein refers to a product or composition which is in the liquid state under the conditions of the processing step in which the stream is formed.

Correspondingly, the expression "vapor stream" as used herein refers to a product or composition which is in the gaseous state under the conditions of the processing step in which the stream is formed.

The expression "reaction zone" as used herein refers to at least one reactor or vessel in which methanol is carbonylated in the presence of a catalyst to form acetic acid at elevated pressure and temperature, i.e., the reactor(s) of a methanol producing plant.

The expression "flash zone" as used herein refers to at least one tank or vessel in which the reaction mixture obtained by carbonylating methanol in the presence of a catalyst to form acetic acid is at least partially depressurized and/or cooled to form a vapor stream and a liquid stream, i.e., the flash tank(s) in the reaction area of a methanol producing plant.

The expression "fractioning zone" as used herein refers to at least one fractioning or distillation column, i.e., the light ends distillation column(s) in the light ends recovery area of an acetic acid producing plant.

The expression "partitioning zone" as used herein refers to at least one phase separation tank or vessel in which a mixture comprising acetic acid, methyl acetate, methyl iodide, and water, is partitioned, i.e., the decanter in the light ends recovery area of an acetic acid producing plant.

Correspondingly, the expressions "partitioning" and "phase separating" which are used herein synonymously refer to causing a mixture comprising acetic acid, methyl acetate, methyl iodide, and water, to form a continuous aqueous phase comprising acetic acid and water, and a continuous organic phase comprising methyl iodide and methyl acetate. In particular, the expression "partitioning" and "phase separating" refer to causing the liquid mixture (D) to form the aqueous phase ($D_A$) and the organic phase ($D_O$).

The expression "innate" as used herein with a view to a chemical compound refers to a chemical compound which is introduced to the process as a starting material, or as a constituent of a starting material stream, which is fed to the reaction zone, as well as a chemical compound which is generated in the process as a product or by-product, e.g., of the carbonylation of methanol in the presence of the catalyst, or of a work-up or purification stage.

Correspondingly, the expression "extraneous" as used herein with a view to a chemical compound refers to a chemical compound which is introduced to the process separately and independent from starting material streams that are fed to the reaction zone. The expression "extraneous" in particular also excludes any chemical compound which is generated in the process as a product or by-product.

Unless specifically indicated otherwise, the expression "heavy phase" refers to the organic, methyl iodide containing phase as, e.g., obtained in the decanter operation of an acetic acid plant. The expression in particular includes the heavy, organic phase ($D_O$) in accordance with this disclosure.

The expressions "OAc" or "AcO" are used herein as abbreviations for the acetate anion, i.e., $H_3CC(=O)O^-$.

The expression "Me" is used herein as an abbreviation for the methyl group.

The expression "acac" is used herein as an abbreviation for acetoacetate anion, i.e., $H_3CC(=O)CH_2C(=O)O^-$.

Unless specifically indicated otherwise, the expression "wt. %" as used herein refers to the percentage by weight of a particular component in the referenced composition.

With respect to all ranges disclosed herein, such ranges are intended to include any combination of the mentioned upper and lower limits even if the particular combination is not specifically listed.

All publications, patent applications, and patents mentioned herein are incorporated by reference in their entirety. In the event of conflict, the present specification, including definitions, is intended to control.

Previously unattainable decanter phase separation at low water light ends overhead composition (LEOC) can now be achieved by manipulation of decanter or LEOC temperature. The present invention provides flexibility to operate at lower water concentration in reaction section with associated decreased energy usage in purification section.

In its broadest aspect, the present disclosure describes a process for producing acetic acid which involves
(a) carbonylating methanol in the presence of a catalyst in a reaction zone to obtain a reaction mixture (A) comprising acetic acid, methyl acetate, methyl iodide, the catalyst, and water;
(b) separating at least a part of the reaction mixture (A) in a flash zone to obtain a liquid stream ($B_L$) comprising the catalyst, and a vapor stream ($B_V$) comprising acetic acid, methyl acetate, methyl iodide, and water, and withdrawing the vapor stream ($B_V$) from the flash zone;
(c) separating the vapor stream ($B_V$) in a fractioning zone to obtain a product stream ($C_P$) comprising acetic acid and a minor amount of water, and an overhead stream ($C_O$) comprising acetic acid, methyl acetate, methyl iodide, and water,
(d) condensing the overhead stream ($C_O$) and forming a liquid mixture (D) which has a water content of at most 10% by weight, an acetic acid content of at least 10% by weight, and which comprises methyl iodide and methyl acetate in a weight ratio of methyl iodide to methyl acetate of at least 1.5:1,
(e) partitioning the liquid mixture (D) in a partitioning zone to obtain a light, aqueous phase ($D_A$) comprising acetic acid, and water, and a heavy, organic phase ($D_O$) comprising methyl iodide, and methyl acetate;

wherein liquid mixture (D) is partitioned at a temperature of from 0 to 35° C.

In general, it has been found that the phase separation in the decanter of an acetic acid process which is conducted under low-water process conditions can be significantly improved and expedited by controlling the temperature of the liquid mixture which is to be partitioned, and by controlling the weight ratio in which methyl iodide and methyl acetate are present in the liquid mixture.

It has been found, surprisingly, that the condensed overhead stream ($C_O$) which is obtained when acetic acid is produced by carbonylating methanol under low water-high acid conditions can be efficiently and thoroughly separated into an aqueous phase ($D_A$) and an organic phase ($D_O$) by forming a liquid mixture (D) which has a water content of at most 10% by weight, an acetic acid content of at least 10% by weight, and which comprises methyl iodide and methyl acetate in a weight ratio of methyl iodide to methyl acetate of at least 1.5:1, and by ensuring that the temperature of the liquid mixture (D) is in a range of from 0 to 35° C. The prompt and efficient phase separation in the decanter of an acetic acid plant operated under low-water process conditions, thus, can be maintained stable by controlling and adjusting the temperature of the decanter, and the ratio of methyl iodide to methyl acetate. The reliable phase separation in the decanter is achieved without the need for additional distillation operations and without upsetting the water balance of the process. Additionally, the prompt and efficient partitioning which is achieved in accordance with the process disclosed herein ensures that the reactor conditions remain stable, and that undesirable by-products can be removed from the process in a simple manner similar to the operations used for that purpose in the acetic acid production under conventional high-water process conditions.

Figure 2:
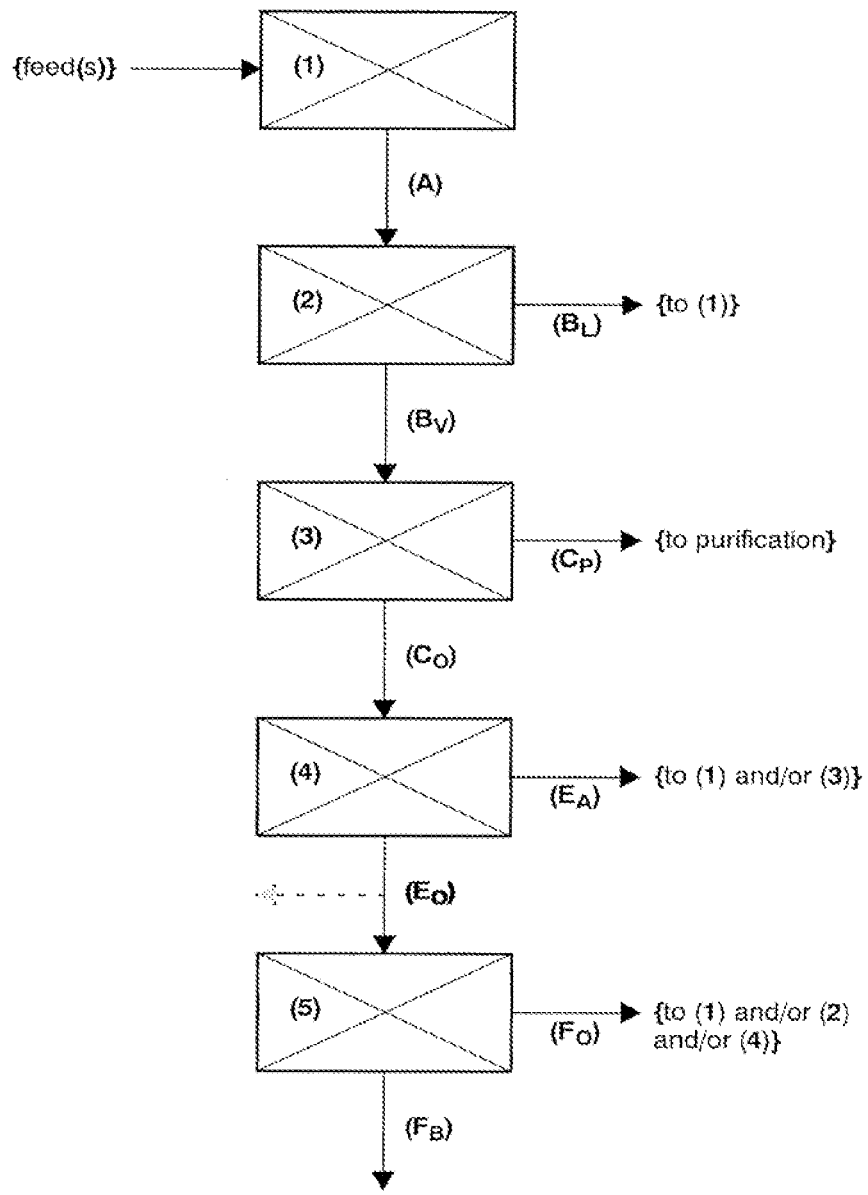
FIG. 2 shows a flow-chart schematically illustrating the flow of the stream(s) involved in the process according to the present disclosure.

The flow charts in FIGS. 1 and 2 schematically illustrate the flow of the streams involved in the process of the present disclosure. Accordingly, the starting materials are fed continuously or batch-wise into the reaction zone (1). At least a part of the reaction mixture (A) which is formed in the reaction zone (1) is withdrawn and is separated, by a flash separation in the flash zone (2), to obtain a liquid stream ($B_L$) comprising the catalyst and, where present, the catalyst stabilizer, and a vapor stream ($B_V$) comprising the acetic acid, methyl acetate, methyl iodide, and water. The liquid stream ($B_L$) is preferably recycled to the reaction zone (1).

The vapor stream ($B_V$) is conveyed to the fractioning zone (3) where it is separated to obtain at least a product stream ($C_P$) comprising acetic acid and a minor amount of water, and an overhead stream ($C_O$) comprising acetic acid, methyl acetate, methyl iodide, and water. Those having ordinary skill will appreciate that further streams (not shown) may be recovered from the fractioning zone (3), e.g., a bottoms stream ($C_B$) comprising any catalyst which may have become entrained in $B_V$. Where applicable, such bottoms stream ($C_B$) may be recycled to the reaction zone (1) (not shown).

The overhead stream ($C_O$) is condensed and a liquid mixture (D) is formed which has a water content of at most 10% by weight, based on the weight of the liquid mixture, an acetic acid content of at least 10% by weight, based on the weight of the liquid mixture, and a weight ratio of methyl iodide to methyl acetate of at least 1.5:1. The liquid mixture (D) is partitioned in a partitioning zone (4), i.e., a decanter, by providing for a temperature of D of from 0 to 35° C., to obtain a light, aqueous phase ($D_A$) comprising acetic acid and water, and a heavy, organic phase ($D_O$) comprising methyl iodide, and methyl acetate.

In general the temperature of D is controlled using a cooling unit or any apparatus that is capable of cooling the liquid mixture as it is being partitioned. The cooling unit may regulate the temperature such that the temperature of D is from 0 to 35° C., from 5 to 35° C., from 10 to 35° C., from 15 to 35° C., from 20 to 35° C., from 25 to 35° C., from 30 to 35° C., from 0 to 30° C., from 0 to 25° C., from 0 to 20° C., from 0 to 15° C., from 0 to 10° C., from 0 to 5° C., or any range in between. In particular, the cooling unit may regulate the temperature such that the temperature of D is about 5° C., about 10° C., about 15° C., about 20° C., about 25° C., about 27° C., about 29° C., about 31° C., about 33° C., about 35° C.

The partitioned phases $D_A$ and $D_O$ are separated to obtain an aqueous stream ($E_A$) and an organic stream ($E_O$).

The aqueous stream ($E_A$) may be recycled, in whole or in part, to the reaction zone (1) and/or the fractioning zone (3). Preferably, the aqueous stream ($E_A$), or a part thereof, which is being recycled is processed to remove impurities and excess water before being reintroduced into the process. Suitable processing methods are known in the art and include, e.g., the methods disclosed in U.S. Pat. No. 5,625,095, U.S. Pat. No. 5,783,731, U.S. Pat. No. 6,143,930, and U.S. Pat. No. 6,339,171. The organic stream ($E_O$) may be recycled, in whole or in part, to the reaction zone (1), the flash zone (2), and/or the partitioning zone (4).

In accordance with the embodiments schematically illustrated in the flow chart FIG. 2, at least a part of the organic stream ($E_O$) is further separated in a distillation zone (5) to obtain an overhead product ($F_O$) comprising methyl iodide, and a bottom product ($F_B$) comprising acetic acid, methyl acetate, and water. The overhead product ($F_O$) may be split with a part of the overhead product ($F_O$) being recycled to the reaction zone (1), and/or the flash zone (2), and another part of the overhead product ($F_O$) being recycled to the partitioning zone (4). The bottom product ($F_B$) may be purged from the process to maintain the water balance of the reaction system, or may be treated further to remove excess water and/or impurities before being recycled to the reaction zone (1), the flash zone (2), and/or the partitioning zone (4) (not shown).

While the process may be performed batch-wise, it is preferable to operate the process continuously.

The carbonylation reaction in accordance with the present disclosure is performed in the presence of a carbonylation catalyst and optionally a catalyst stabilizer. Suitable carbonylation catalysts include those known in the acetic acid industry. Examples of suitable carbonylation catalysts include rhodium catalysts and iridium catalysts.

Suitable rhodium catalysts are described, for example, in U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are described, for example, in U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-$ $H^+$, $[Ir(CO)_2I_2]^-H^+$, $[Ir(CH_3)I_3(CO)_2]^-H^-$, $Ir_4(CO)_{12}$, $IrCl_3 \times 4H_2O$, $IrBr_3 \times 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

The reaction rate depends upon the concentration of the catalyst in the reaction mixture (A). The catalyst concentration normally is from about 1.0 mmol to about 100 mmol catalyst per liter (mmol/l) of (A). In some embodiments the catalyst concentration is at least 2.0 mmol/l, or at least 5.0 mmol/l, or at least 7.5 mmol/l. In some embodiments the catalyst concentration is at most 75 mmol/l, or at most 50 mmol/l, or at least 25 mmol/l. In particular embodiments, the catalyst concentration is from about 2.0 to about 75 mmol/l, or from about 2.0 to about 50 mmol/l, or from about 5.0 to about 25 mmol/l.

In some embodiments, the reaction is performed in the presence of a catalyst stabilizer. Suitable catalyst stabilizers include those known to the industry. In general, there are two types of catalyst stabilizers. The first type of catalyst stabilizer is metal iodide salt, i.e., a iodide of a metal of Group 1 or 2 such as lithium iodide. The second type of catalyst stabilizer is a non-salt stabilizer. Preferred non-salt stabilizers are pentavalent Group 15 oxides. See U.S. Pat. No. 5,817,869. Phosphine oxides are more preferred. Triphenylphosphine oxides are most preferred.

The amount of metal iodide, when used, generally is such that a concentration of from about 1 to about 20 wt. % (about 0.1 to about 1.75 M) of the metal iodide is present in the reaction mixture. More preferably, this optional component is present in the reaction mixture in an amount of from about 5 to about 10 wt. % which corresponds to a molarity range of from about 0.5 to about 1.0 M.

The amount of pentavalent Group 15 oxide, when used, generally is such that its concentration to rhodium is greater than about 60:1. Preferably, the concentration of the pentavalent Group 15 oxide to rhodium is from about 60:1 to about 500:1. In some embodiments, from about 0.1 to about 3 M of the pentavalent Group 15 oxide is present in the reaction mixture. More preferably, from about 0.15 to about 1.5 M, or from 0.25 to 1.2 M, of the pentavalent Group 15 oxide is present in the reaction mixture.

In other embodiments, the reaction is performed in the absence of a stabilizer selected from the group of metal iodides and pentavalent Group 15 oxides. In further embodiments, the catalyst stabilizer may be formed by reacting ($B_V$) with an alkylimidazole as disclosed in application Ser. No. 13/088,145 filed on Apr. 15, 2011.

The carbonylation reaction is performed in the presence of a finite amount of water. Preferably, the concentration of water which is present in the reaction mixture (A) amounts to not more than about 10 wt. % based on the total weight of the reaction mixture (A). More preferably, the water concentration is at most 6 wt. %, or at most 4 wt. %, or at most 2 wt. %. In some embodiments, the concentration of water in the reaction mixture is at least 0.1 wt. %, or at least 0.5 wt. %, or at least 1 wt. %. Accordingly, the water concentration in the reaction mixture may range from 0.1 to 10 wt. %, or from 0.1 to 6 wt. %, or from 0.1 to 4 wt. %, or from 0.1 to 2 wt. %. Alternatively, the water concentration in the reaction mixture may range from 0.5 to 10 wt. %, or from 0.5 to 6 wt. %, or from 0.5 to 4 wt. %, or from 0.5 to 2 wt. %. Similarly, the water concentration in the reaction mixture may range from 1 to 10 wt. %, or from 1 to 6 wt. %, or from 1 to 4 wt. %, or from 1 to 2 wt. %.

The reaction is preferably performed in the presence of methyl acetate as a rate promoter. Methyl acetate may be formed in situ. Normally, methyl acetate will be added as a starting material to the reaction mixture. Preferably, the concentration of methyl acetate in the reaction mixture (A) may be from about 2 wt. % to about 20 wt. % based on the total weight of the reaction mixture (A). More preferably, the concentration of methyl acetate may be from about 2 wt. % to about 16 wt. %. Most preferably, the concentration of methyl acetate is from about 2 wt. % to about 8 wt. %. Alternatively, methyl acetate or a mixture of methyl acetate and methanol from by-product streams of the hydrolysis/methanolysis of polyvinyl acetate can be used for the carbonylation reaction.

The reaction is performed in the presence of methyl iodide. Methyl iodide acts as a catalyst promoter. Preferably, the concentration of methyl iodide is from about 0.6 wt. % to about 36 wt. % based on the total weight of the reaction mixture (A). More preferably, the concentration of methyl iodide is from about 4 wt. % to about 24 wt. %. Most preferably, the concentration of methyl iodide is from about 6 wt. % to about 20 wt. %. Alternatively, methyl iodide can be generated in the carbonylation reactor or reaction zone (1) by adding hydrogen iodide.

Hydrogen may also be fed into the reaction zone (1). Addition of hydrogen can enhance the carbonylation efficiency. Preferably, the concentration of hydrogen is from about 0.1 mol % to about 5 mol % of carbon monoxide in the reaction zone (1). More preferably, the concentration of hydrogen is from about 0.3 mol % to about 3 mol % of carbon monoxide in the reaction zone (1).

Methanol and carbon monoxide are fed to the reaction zone (1). The methanol feed to the carbonylation reaction can come from a syngas-methanol facility or any other source. Methanol does not react directly with carbon monoxide to form acetic acid. It is converted to methyl iodide by the hydrogen iodide present in the reaction zone (1) and then reacts with carbon monoxide and water to give acetic acid and regenerate hydrogen iodide. Carbon monoxide not only becomes part of the acetic acid molecule, but it also plays an important role in the formation and stability of the active catalyst.

The carbonylation reaction is preferably performed at a temperature of about 120° C. to about 250° C. More preferably, the reaction is performed at a temperature of about 150° C. to about 200° C.

The carbonylation reaction is preferably performed under a pressure of about 200 psig to about 2,000 psig. More preferably, the reaction is performed under a pressure of about 300 psig to about 500 psig.

The flash zone (2) is preferably maintained at a pressure below that of the reaction zone (1), typically at a pressure of from about 10 to 100 psig. The flash zone (2) is preferably maintained at a temperature of from about 100 to 160° C.

The vapor stream ($B_V$) comprising the acetic acid, methyl acetate, methyl iodide, and water, is conveyed from the flash zone (2) to the fractioning zone (3) where it is separated to obtain a product stream ($C_P$) comprising acetic acid and a minor amount of water, and an overhead stream ($C_O$) comprising acetic acid, methyl acetate, methyl iodide, and water. The product stream ($C_P$) is normally subjected to further purification in a manner known per se.

The fractioning zone (3) is normally embodied by one or more distillation columns. Those having ordinary skill in the art will readily appreciate that the temperature and pressure conditions maintained in the fractioning zone (3) will depend upon the number and type of distillation columns, and on the distillation stages of the column or columns. Illustratively, when the fractioning zone (3) is embodied by one distillation column, the column preferably has at least 10, more preferably at least 14, or at least 18, actual stages. In such a set-up, the distillation column is preferably operated at an overhead pressure within the range of 20 psia (1.4 kg/cm$^2$) to 40 psia (2.8 kg/cm$^2$), or from 25 to 35 psia, and at a bottom pressure of 25 from psia to 45 psia, or from 30 psia to 40 psia. Correspondingly, the overhead temperature is of from 95° C. to 135° C., or from 100° C. to 125° C., or from 110° C. to 120° C., and the bottom temperature is of from 115° C. to 155° C., or from 125° C. to 135° C.

The overhead stream ($C_O$) is recovered from the fractioning zone (3) and is condensed, e.g., by cooling.

The composition of the condensed overhead stream ($C_O$) may vary, e.g., depending on the composition of the reaction mixture (A) as well as the set up and the conditions in the flash zone (2) and in the fractioning zone (3). In general, the condensed overhead stream will comprise at most about 15 wt. % of water, at least about 10 wt. % of acetic acid, up to about 45 wt. % methyl acetate, and at least about 25 wt. % of methyl iodide.

In some embodiments of the process, the overhead stream ($C_O$) may have a water content of at most 15 wt. %, or at most 12 wt. %, or at most 10 wt. %, or at most 8 wt. %. Generally, the overhead stream ($C_O$) has a water content of at least 0.5 wt. %, or at least 1 wt. %, or at least 2 wt. %, or at least 5 wt. %. In particular embodiments, the water content of the overhead stream ($C_O$) may range from 0.5 wt. % to 15 wt. %, or from 0.5 wt. % to 12 wt. %, or from 0.5 wt. % to 10 wt. %, or from 0.5 wt. % to 8 wt. %. In other embodiments, the water content of the overhead stream ($C_O$) may range from 1 wt. % to 15 wt. %, or from 1 wt. % to 12 wt. %, or from 1 wt. % to 10 wt. %, or from 1 wt. % to 8 wt. %. In other embodiments, the water content of the overhead stream ($C_O$) may range from 2 wt. % to 15 wt. %, or from 2 wt. % to 12 wt. %, or from 2 wt. % to 10 wt. %, or from 2 wt. % to 8 wt. %. In yet further embodiments, the water content of the overhead stream ($C_O$) may range from 5 wt. % to 15 wt. %, or from 5 wt. % to 12 wt. %, or from 5 wt. % to 10 wt. %, or from 5 wt. % to 8 wt. %.

In general, the overhead stream ($C_O$) may have an acetic acid content of at least 10 wt. %, or at least 12 wt. %, or at least 15 wt. %. Normally, the acetic acid content of the overhead stream ($C_O$) will not exceed 35 wt. %, or 30 wt. %, or 25% wt. %. Accordingly, the acetic acid content of the overhead stream ($C_O$) may range from 10 to 35 wt. %, or from 12 to 35 wt. %, or from 15 to 35 wt. %. Alternatively, the acetic acid content of the overhead stream ($C_O$) may range from 10 to 30 wt. %, or from 12 to 30 wt. %, or from 15 to 30 wt. %. Further, the acetic acid content of the overhead stream ($C_O$) may range from 10 to 25 wt. %, or from 12 to 25 wt. %, or from 15 to 25 wt. %.

The concentration of methyl acetate in the overhead stream ($C_O$) normally will be at most 45 wt. %, or at most 40 wt. %, or at most 35 wt. %, or at most 30 wt. %, and generally will be not less than 2 wt. %, or 5 wt. %, or 10 wt. %. Accordingly, methyl acetate concentration in the overhead stream ($C_O$) may range from 2 to 45 wt. %, or from 2 to 40 wt. %, or from 2 to 35 wt. %, or from 2 to 30 wt. %. Correspondingly, methyl acetate concentration in the overhead stream ($C_O$) may range from 5 to 45 wt. %, or from 5 to 40 wt. %, or from 5 to 35 wt. %, or from 5 to 30 wt. %. Alternatively, methyl acetate concentration in the overhead stream ($C_O$) may range from 10 to 45 wt. %, or from 10 to 40 wt. %, or from 10 to 35 wt. %, or from 10 to 30 wt. %.

Methyl iodide is present in the overhead stream ($C_O$) generally in at least 25 wt. %, or at least 35 wt. %, or at least 45 wt. %, or at least 50 wt. %, and normally will not exceed 93 wt. %, or 90 wt. %, or 75 wt. %. Accordingly, the methyl iodide concentration of the overhead stream ($C_O$) may range from 25 to 93 wt. %, or from 35 to 93 wt. %, or from 45 to 93 wt. %, or from 50 to 93 wt. %. Correspondingly, the methyl iodide concentration of the overhead stream ($C_O$) may range from 25 to 90 wt. %, or from 35 to 90 wt. %, or from 45 to 90 wt. %, or from 50 to 90 wt. %. Alternatively, the methyl iodide concentration of the overhead stream ($C_O$) may range from 25 to 75 wt. %, or from 35 to 75 wt. %, or from 45 to 75 wt. %, or from 50 to 75 wt. %.

Those having skill in the art will appreciate that the overhead stream ($C_O$) additionally may comprise normally gaseous constituents such as hydrogen, carbon monoxide and carbon dioxide, as well as carbonyl components which are formed as by-products of the reaction. Non-condensable, normally gaseous constituents of the overhead stream ($C_O$) may be vented (not shown).

The process in accordance with the present disclosure achieves prompt and efficient phase separation by forming a liquid mixture (D) which has a water content of at most 10 wt. %, an acetic acid content of at least 10 wt. %, and which comprises methyl iodide and methyl acetate in a weight ratio of at least 1.5:1, and by performing the phase separation at a temperature of from 0 to 35° C.

Preferably, the water which is present in the liquid mixture (D) exclusively is innate water. The liquid mixture (D) may be formed prior to, during, or after condensation of the overhead stream ($C_O$), prior to or during conveying the condensed overhead stream ($C_O$) to the separation zone (4), or in the separation zone (4). As the partitioning time and the residence time of the mixture in the separation zone (4) preferably be low, it may be preferable to form the liquid mixture (D) prior to, during, or after condensation of the overhead stream ($C_O$), prior to or during conveying the condensed overhead stream ($C_O$) to the separation zone (4).

In accordance with some embodiments, the liquid mixture (D) is formed by adding to $C_O$ extraneous or innate methyl iodide, acetic acid, or mixtures thereof, optionally in combination with innate water, provided that the resultant composition of D contains at most 10 wt. % of water and at least 10 wt. % of acetic acid, and that methyl iodide and methyl acetate are present in the liquid mixture in a weight ratio of at least 1.5:1.

Suitable sources for innate methyl iodide, acetic acid, and mixtures thereof, optionally in combination with innate water, include for example, the streams $E_A$ and $E_O$, and preferably $F_O$. When providing the weight ratio of methyl iodide to methyl acetate of the liquid mixture (D) based on innate methyl iodide, the suitable concentration of methyl iodide in D conveniently is adjusted by controlling the amount of $E_O$ and $F_O$, respectively, which is combined with $C_O$, and/or by controlling the amount of $E_O$ which is conveyed to the distillation zone (5). In particular embodiments of the continuous procedure, the amounts and the concentration of the recycle streams $E_O$ and $F_O$ are controlled such as to establish a steady state concentration of methyl iodide in $C_O$ of at least about 45 wt. %, based on the weight of the $C_O$ condensate. Thus, under steady state conditions, the liquid mixture (D) may be formed by condensing $C_O$. Alternatively or additionally, a part of the stream feeding methyl iodide into the reaction zone (1) may be split off, and the split stream may serve as an extraneous source of methyl iodide for forming the liquid mixture (D). This approach may be employed prior to, during, or after the period of the process in which steady state conditions are or have been established.

In a particular implementation of the process, at least a part of the organic stream ($E_O$) is separated to obtain an overhead product ($F_O$) comprising methyl iodide and a bottom product ($F_B$) comprising acetic acid, methyl acetate, and water, and the overhead product ($F_O$) is recycled to the reaction zone (1). Advantageously, the amount of the organic stream ($E_O$) and the separation thereof may be adjusted such as to provide a steady state methyl iodide content of $C_O$ at the desired level. The separation of the organic stream ($E_O$) is effected in the distillation zone (5). The distillation zone (5) is normally embodied by one or more distillation columns. Those having ordinary skill in the art will appreciate that the temperature and pressure conditions maintained in the distillation zone (5) will depend upon the number and type of the distillation columns, and on the distillation stages of the column or columns.

The weight ratio of methyl iodide to methyl acetate in the liquid mixture (D) should be maintained at a level of at least 1.5:1. In general, it has been found that increasing the weight ratio of methyl iodide to methyl acetate improves the phase separation. Thus, in some embodiments, the weight ratio of methyl iodide to methyl acetate in the liquid mixture (D) is at least 2:1, or is at least 2.5:1, or is at least 3:1. In other embodiments, the weight ratio of methyl iodide to methyl acetate in the liquid mixture (D) is at least 3.5:1, or is at least 4.5:1, or is at least 5:1. The phase separation improves, and the time necessary for phase separating the liquid mixture (D) decreases, as the weight ratio of methyl iodide to methyl acetate increases. Thus, in some embodiments the weight ratio of methyl iodide to methyl acetate in the liquid mixture (D) may be up to 600:1, or up to 450:1, or up to 350:1. However, in some embodiments large amounts of methyl iodide would be required in order to arrive at a weight ratio of 350:1 or more. Under those circumstances, the significantly increased volume of (D) may increase the over-all load of, e.g., the partitioning vessel (4) and the distillation zone (5), as well as the load on down-stream equipment such as pumps. Also, as the volume of (D) is increased significantly, more energy may be required to control the temperature. Thus, for reasons of process economy, it may be preferable to maintain the weight ratio of methyl iodide to methyl acetate in the liquid mixture (D) at a level of at most 15:1, or at most 10:1, or at most 8:1. Accordingly, in some embodiments the weight ratio of methyl iodide to methyl acetate may be from 1.5-15:1, or from 2-15:1, or from 2.5-15:1, or from 3-15:1. Alternatively, the weight ratio of methyl iodide to methyl acetate may be from 1.5-10:1, or from 2-10:1, or from 2.5-10:1, or from 3-10:1. Additionally, the weight ratio of methyl iodide to methyl acetate may be from 1.5-8:1, or from 2-8:1, or from 2.5-8:1, or from 3-8:1.

Generally, the liquid mixture (D) comprises methyl iodide in at least 30 wt. %, or at least 40 wt. %, or at least 45 wt. %, or at least 50 wt. %, and the methyl iodide content normally will not exceed 93 wt. %, or 90 wt. %, or 75 wt. %. Accordingly, the methyl iodide concentration of the liquid mixture (D) may range from 30 to 93 wt. %, or from 40 to 93 wt. %, or from 45 to 93 wt. %, or from 50 to 93 wt. %. Correspondingly, the methyl iodide concentration of the liquid mixture (D) may range from 30 to 90 wt. %, or from 40 to 90 wt. %, or from 45 to 90 wt. %, or from 50 to 90 wt. %. Alternatively, the methyl iodide concentration of the liquid mixture (D) may range from 30 to 75 wt. %, or from 40 to 75 wt. %, or from 45 to 75 wt. %, or from 50 to 75 wt. %.

The amount of water which is present in the liquid mixture (D) preferably is kept at a low level to ensure that low-water conditions of the process are maintained stable. Accordingly, it is preferred that the amount in which water is present in the liquid mixture (D) be as low as possible. Therefore, the amount of water in the liquid mixture (D) preferably is at most 9 wt. %, or at most 8 wt. %, or at most 7.5 wt. %. In further particular embodiments, the amount of water in the liquid mixture (D) may be at most 5 wt. %, or at most 4 wt. %, or at most 2.5 wt. %. Accordingly, in some embodiments the liquid mixture (D) may comprise water in amounts of from 2.5 to 9 wt. %, or from 4 to 9 wt. %, or from 5 to 9 wt. %. Alternatively, the liquid mixture (D) may comprise water in amounts of from 2.5 to 8 wt. %, or from 4 to 8 wt. %, or from 5 to 8 wt. %. Additionally, the water content of the liquid mixture (D) may range from 2.5 to 7.5 wt. %, or from 4 to 7.5 wt. %, or from 5 to 7.5 wt. %.

As stated at the outset, the partitioning time, i.e., the time which is necessary for the liquid mixture to form the continuous organic phase and the continuous aqueous phase in the decanter, is critical to the overall performance of the acetic acid process. That is, the partitioning time for the liquid mixture has to be shorter than the residence time of the mixture in the decanter. It has now been found, surprisingly, that the partitioning time of the liquid mixture under low-water conditions is distinctly influenced by the water content of the liquid mixture and by the temperature thereof. On the one hand, as the water content of the liquid mixture (D) is decreased, the partitioning time increases. On the other hand, as the temperature of the liquid mixture (D) is decreased, the partitioning time decreases. Moreover, it has been found that the temperature dependence of the partitioning time becomes more pronounced as the water content of the liquid mixture is decreased.

Figure 3:
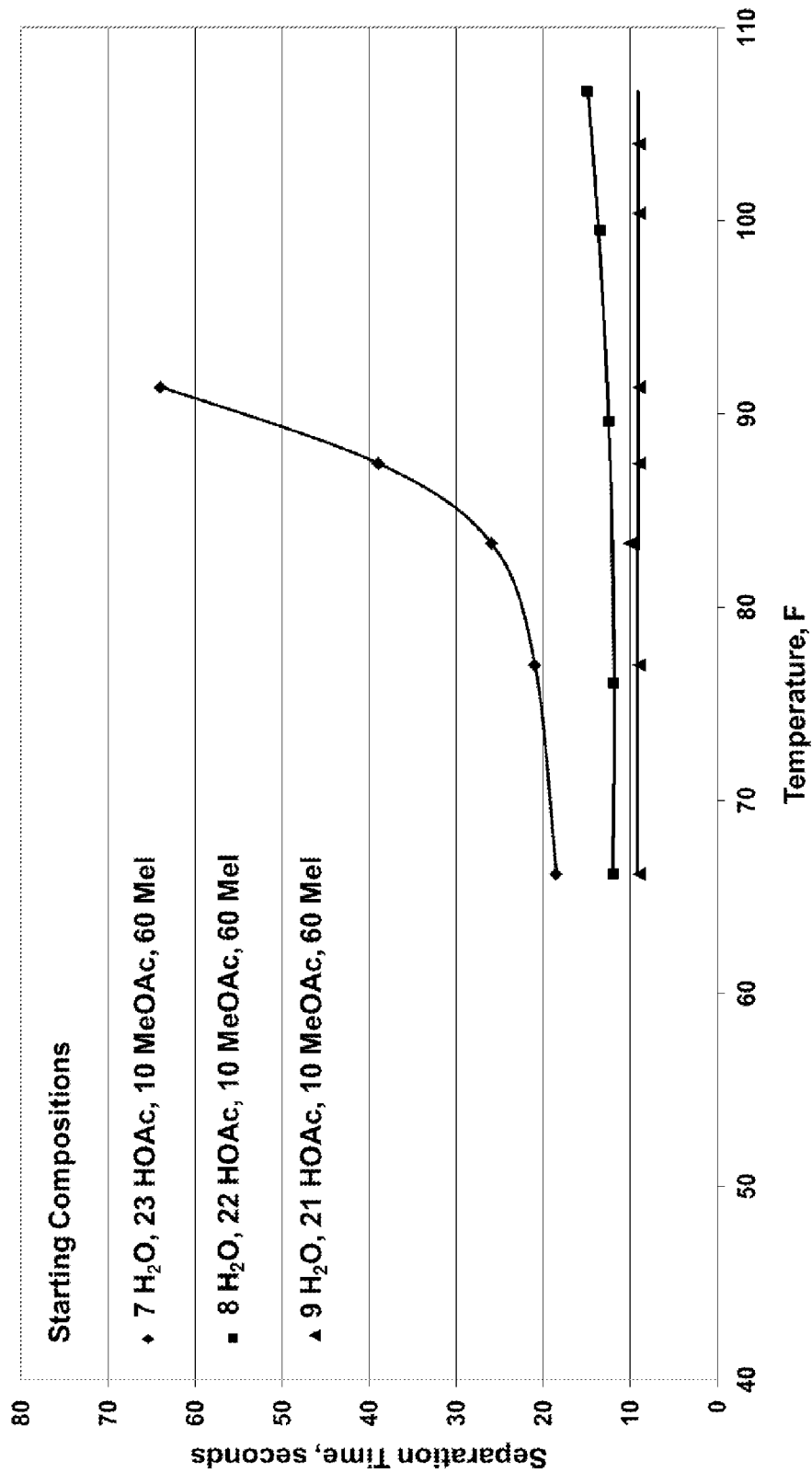
FIG. 3 illustrates the influence of water content and temperature on the partitioning time of mixtures comprising acetic acid, methyl acetate, methyl iodide, and water, in the process according to the present disclosure.

The relation between partitioning time, water content, and temperature of an illustrative liquid mixtures (D) is shown in FIG. 3. As can be seen, the partitioning time of the liquid mixture comprising about 9 wt. % of water did not vary significantly within a temperature range of from about 65 F (about 18° C.) to about 100 F (about 38° C.). In the case of the liquid mixture comprising about 8 wt. % of water, the partitioning time was about 15% faster at about 65 F (about 18° C.) than at about 100 F (about 38° C.). The illustrative mixture comprising about 7 wt. % of water which required more than 60 sec. to phase separate at about 90 F (about 32° C.), phase separated in less than 20 sec. at about 65 F (about 18° C.). Thus, those having ordinary skill in the art will appreciate that the temperature which provides the optimum partitioning time for a specific liquid mixture (D) will depend to a large extent upon the amount of water which is present in the liquid mixture (D). More specifically, the optimum temperature will be at the lower end of the temperature range when the water content of the liquid mixture (D) is low, and may be at the higher end of the temperature range when the water content of the liquid mixture (D) is high.

In general, the liquid mixture (D) may have an acetic acid content of at least 10 wt. %, or at least 12 wt. %, or at least 15 wt. %. Normally, the acetic acid content of the liquid mixture (D) will not exceed 35 wt. %, or 30 wt. %, or 25% wt. %. Accordingly, the acetic acid content of the liquid mixture (D) may range from 10 to 35 wt. %, or from 12 to 35 wt. %, or from 15 to 35 wt. %. Alternatively, the acetic acid content of the liquid mixture (D) may range from 10 to 30 wt. %, or from 12 to 30 wt. %, or from 15 to 30 wt. %. Further, the acetic acid content of the liquid mixture (D) may range from 10 to 25 wt. %, or from 12 to 25 wt. %, or from 15 to 25 wt. %.

The concentration of methyl acetate in the liquid mixture (D) normally will be at most 45 wt. %, or at most 40 wt. %, or at most 35 wt. %, or at most 30 wt. %, and generally will be not less than 2 wt. %, or 5 wt. %, or 10 wt. %. Accordingly, methyl acetate concentration in the liquid mixture (D) may range from 2 to 45 wt. %, or from 2 to 40 wt. %, or from 2 to 35 wt. %, or from 2 to 30 wt. %. Correspondingly, methyl acetate concentration in the liquid mixture (D) may range from 5 to 45 wt. %, or from 5 to 40 wt. %, or from 5 to 35 wt. %, or from 5 to 30 wt. %. Alternatively, methyl acetate concentration in the liquid mixture (D) may range from 10 to 45 wt. %, or from 10 to 40 wt. %, or from 10 to 35 wt. %, or from 10 to 30 wt. %.

In accordance with some embodiments of the process disclosed herein, the liquid mixture (D) may comprise
  (i) from 30 to 84.9 wt. % of methyl iodide,
  (ii) from 10 to 25 wt. % of acetic acid,
  (iii) from 5 to 35 wt. % of methyl acetate, and
  (iv) from 0.1 to 10 wt. % of water,
with the weight percentages in each case being based on the total weight of the components (i) to (iv).

In accordance with other embodiments of the process disclosed herein, the liquid mixture (D) may comprise
  (i) from 37 to 79.5 wt. % of methyl iodide,
  (ii) from 15 to 30 wt. % of acetic acid,
  (iii) from 5 to 25 wt. % of methyl acetate, and
  (iv) from 0.5 to 8 wt. % of water,
with the weight percentages in each case being based on the total weight of the components (i) to (iv).

In accordance with further embodiments of the process disclosed herein, the liquid mixture (D) may comprise
  (i) from 37 to 79 wt. % of methyl iodide,
  (ii) from 10 to 30 wt. % of acetic acid,
  (iii) from 10 to 25 wt. % of methyl acetate, and
  (iv) from 1 to 8 wt. % of water,
with the weight percentages in each case being based on the total weight of the components (i) to (iv).

In some embodiments of the process disclosed herein, the liquid mixture (D) may comprise
  (i) from 40 to 85 wt. % of methyl iodide,
  (ii) from 10 to 30 wt. % of acetic acid,
  (iii) from 4 to 22 wt. % of methyl acetate, and
  (iv) from 1 to 8 wt. % of water,
with the weight percentages in each case being based on the total weight of the components (i) to (iv).

In a further particular implementation of the process, partitioning of the liquid mixture (D) is further facilitated by forming a liquid mixture (D) which further comprises from 0.1 to 15 wt. % of alkanes, based on the weight of the liquid mixture (D), as disclosed in general and in particular in U.S. patent application Ser. No. 13/713,930, the contents of which are incorporated herein by reference in its entirety.

A further aspect of the present disclosure employs the principles addressed in the foregoing and provides for a method of expediting phase separation of a mixture comprising at least 10% by weight of acetic acid, at least 5% by weight of methyl acetate, at least 20% by weight of methyl iodide, and at most 10% by weight of water, which method comprises
  (a) reducing the temperature of the liquid mixture, and/or
  (b) adjusting the weight ratio of methyl iodide and methyl acetate in the liquid mixture to a weight ratio of methyl iodide to methyl acetate of at least 1.5:1.

Depending on the water content of the liquid mixture, the temperature may be reduced to be of from 0 to 35° C., or from 0 to 30° C., or from 0 to 25° C., or from 0 to 20° C.

The weight ratio of methyl iodide and methyl acetate in the liquid mixture is generally adjusted by adding appropriate amounts of methyl iodide to the liquid mixture.

In particular embodiments, the liquid mixture comprises at most 9 wt. %, or at most 8.5 wt. %, of water.

The method is specifically suited to expedite the phase separation of mixtures comprising, consisting essentially of, or consisting of
(i) from 25 to 87.5% by weight of methyl iodide,
(ii) from 10 to 25% by weight of acetic acid,
(iii) from 2 to 35% by weight of methyl acetate, and
(iv) from 0.5 to 15% by weight of water,
the weight percentages in each case being based on the total weight of the components (i) to (iv).

In some embodiments, the mixtures to be separated comprise, consist essentially of, or consist of
(i) from 30 to 84.5% by weight of methyl iodide,
(ii) from 12 to 25% by weight of acetic acid,
(iii) from 5 to 35% by weight of methyl acetate, and
(iv) from 0.5 to 10% by weight of water,
the weight percentages in each case being based on the total weight of the components (i) to (iv).

In further embodiments, the mixtures to be separated comprise, consist essentially of, or consist of
(i) from 35 to 81.5% by weight of methyl iodide,
(ii) from 12 to 25% by weight of acetic acid,
(iii) from 5 to 30% by weight of methyl acetate, and
(iv) from 1 to 10% by weight of water,
the weight percentages in each case being based on the total weight of the components (i) to (iv).

In some embodiments of the method, the weight ratio of acetic acid to water in the mixture to be separated is at least 1.5:1, or at least 3:1, or at least 5:1, or at least 10:1.

The process in accordance with the present disclosure significantly at least improves the quality of phase separation and, in some instances, allows phase separation of mixtures which fail to phase separate without control of the temperature and the methyl iodide to methyl acetate ratio. The quality of the phase separation is improved at least in that phase separation in accordance with the processes disclosed herein occurs faster than would be the case at a higher temperature and/or at a weight ratio of methyl iodide to methyl acetate below 1.5:1. With a view to the acetic acid production, the reduced time which is required to achieve partitioning decreases the residence time in the decanter which is necessary and, thus, allows that methyl iodide is recycled at a higher rate. The higher recycle rate of methyl iodide which is made possible by the process in accordance with the present disclosure, in turn, results in a higher steady state concentration of methyl iodide in the reaction zone, thus, allowing for the production of acetic acid to be conducted at higher feed rates.

Additionally, the process in accordance with the present disclosure improves the quality of phase separation in terms of the distribution of acetic acid between the aqueous and the organic phase. With a view to the acetic acid production this means that the amount of the acetic acid which is recycled to the process via the aqueous phase ($D_A$) is increased, whereas the amount of acetic acid which may be removed from the process via the bottom product ($F_B$) is reduced.

The process for producing acetic acid in accordance with the present disclosure therefore allows a more efficient use of starting materials and energy resources.

Moreover, the processes in accordance with the present disclosure significantly improve the reliability of the phase separation. With a view to the acetic acid production, the process prevents that the liquid mixture (D) remains in a single phase, and also prevents that the organic phase becomes "diluted" with acetic acid and water. Accordingly, the process stabilizes the water balance in the reactor and avoids that critical conditions occur which would necessitate reactor shut-down.

The following investigations and examples are intended to be illustrative only, and are not intended to be, nor should they be construed as, limiting the scope of the present invention in any way.

EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Effect of Temperature and Water Content on Partitioning Time

Predetermined amounts of methyl iodide, acetic acid, methyl acetate and water were intimately mixed at various temperatures between 65° F. (18.3° C.) and 110° F. (43.3° C.), and were allowed to settle at the respective temperature. The time necessary for phase separation was determined. The results of the investigations are depicted in FIG. 3.

As can be seen in FIG. 3, the partitioning time increased as the water content of the liquid mixture was decreased whereas the partitioning time decreased as the temperature of the liquid mixture was decreased. The data depicted in FIG. 3 further show that the temperature dependence of the partitioning time became more pronounced as the water content of the liquid mixture was decreased. The partitioning time of the liquid mixture 1.1 composed of about 9 wt. % of water, 21 wt. % of acetic acid, 10 wt. % methyl acetate and 60 wt. % methyl iodide did not vary significantly within a temperature range of from about 65 F (about 18° C.) to about 100 F (about 38° C.). In the case of the liquid mixture 1.2 which was composed of about 8 wt. % of water, 22 wt. % of acetic acid, 10 wt. % methyl acetate and 60 wt. % methyl iodide, the phases separated about 15% faster at about 65 F (about 18° C.) than at about 100 F (about 38° C.). The mixture 1.3 which was composed of about 7 wt. % of water 23 wt. % of acetic acid, 10 wt. % methyl acetate and 60 wt. % methyl iodide did not phase separate at about 100 F (about 38° C.), and more than 60 sec. were required to phase separate at about 90 F (about 32° C.). However, when the temperature of the mixture was reduced to about 65 F (about 18° C.), phase separation occurred in less than 20 sec.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A process for producing acetic acid which comprises:
   (a) carbonylating methanol in the presence of a catalyst in a reaction zone to obtain a reaction mixture (A) comprising acetic acid, methyl acetate, methyl iodide, the catalyst, and water;
   (b) separating at least a part of the reaction mixture (A) in a flash zone to obtain a liquid stream ($B_L$) comprising the catalyst, and a vapor stream ($B_V$) comprising acetic acid, methyl acetate, methyl iodide, and water, and withdrawing the vapor stream ($B_V$) from the flash zone;
   (c) separating the vapor stream ($B_V$) in a fractioning zone to obtain a product stream ($C_P$) comprising acetic acid and a minor amount of water, and an overhead stream ($C_O$) comprising acetic acid, methyl acetate, methyl iodide, and water,
   (d) condensing the overhead stream ($C_O$) and forming a liquid mixture (D) which has a water content of at most 10% by weight, an acetic acid content of at least 10% by weight, and which comprises methyl iodide and methyl acetate in a weight ratio of methyl iodide to methyl acetate of at least 1.5:1,
   (e) partitioning the liquid mixture (D) in a partitioning zone to obtain a light, aqueous phase ($D_A$) comprising acetic acid, and water, and a heavy, organic phase ($D_O$) comprising methyl iodide, and methyl acetate;
   wherein the liquid mixture (D) is partitioned at a temperature of from 0 to 35° C. wherein the liquid mixture (D) comprises
   (i) from 30 to 84.9% by weight of methyl iodide,
   (ii) from 10 to 25% by weight of acetic acid,
   (iii) from 5 to 35% by weight of methyl acetate, and
   (iv) from 0.1 to 10% by weight of water,
   the weight percentages in each case being based on the total weight of the components (i) to (iv).

2. The process of claim 1, wherein the temperature of the liquid mixture (D) is from 5 to 30° C.

3. The process of claim 2, wherein the temperature of the liquid mixture (D) is at most 27° C.

4. The process of claim 1, wherein the water present is the liquid mixture is innate water.

5. The process of claim 4, wherein the liquid mixture (D) comprises from 0.1 to 8.5% by weight of water.

6. The process of claim 5, wherein the liquid mixture (D) comprises at most 7.5% by weight of water.

7. The process of claim 1, wherein the liquid mixture (D) comprises at least 15% by weight of acetic acid.

8. The process of claim 1, wherein the weight ratio of methyl iodide to methyl acetate in the liquid mixture (D) is at least 2:1.

9. The process of claim 1, wherein the liquid mixture (D) comprises at most 35% by weight of methyl acetate.

10. The process of claim 9, wherein the liquid mixture (D) comprises at least 30% by weight of methyl iodide.

11. The process of claim 1, wherein the weight ratio of methyl iodide to methyl acetate of the liquid mixture (D) is provided by adding to $C_O$ extraneous or innate methyl iodide.

12. The process of claim 1, further comprising separating the partitioned phases $D_A$ and $D_O$ to obtain an aqueous stream ($E_A$) and an organic stream ($E_O$), and providing the weight ratio of methyl iodide to methyl acetate of D by directly or indirectly recycling at least a part of the organic stream ($E_O$) to step (d).

13. The process of claim 12, which comprises separating at least a part of the organic stream ($E_O$) to obtain an overhead product ($F_O$) comprising methyl iodide, and a bottom product ($F_B$) comprising acetic acid, methyl acetate, and water, and recycling at least a part of the overhead product ($F_O$) to step (d).

14. The process of claim 1, wherein the partitioning zone is equipped with external or internal cooling means.

15. A method of expediting the phase separation of a liquid mixture comprising at least 10% by weight of acetic acid, at least 5% by weight of methyl acetate, at least 20% by weight of methyl iodide and at most 10% by weight of water, which comprises
   (a) reducing the temperature of the liquid mixture, and
   (b) adjusting the weight ratio of methyl iodide and methyl acetate in the liquid mixture to a weight ratio of methyl iodide to methyl acetate of at least 1.5:1 wherein the temperature of the liquid mixture is reduced to be of from 0 to 35° C.

16. The method of claim 15, wherein the weight ratio of methyl iodide and methyl acetate is adjusted by adding appropriate amounts of methyl iodide to the liquid mixture.

17. The method claim 16, wherein the liquid mixture comprises at most 8.5% by weight of water.

* * * * *